United States Patent [19]

Moser et al.

[11] 4,003,247
[45] Jan. 18, 1977

[54] TORSIONAL OSCILLATION APPARATUS

[75] Inventors: Kurt Moser, Fribourg; Beat Hochli, Bern, both of Switzerland

[73] Assignee: Lonza Ltd., Gampel, Switzerland

[22] Filed: Oct. 22, 1975

[21] Appl. No.: 624,894

[30] Foreign Application Priority Data

Oct. 31, 1974 Switzerland ............... 14575/74

[52] U.S. Cl. ................................................ 73/99
[51] Int. Cl.² ...................................... G01N 3/32
[58] Field of Search .............. 73/99, 383, 70.1; 58/131

[56] References Cited

UNITED STATES PATENTS

| | | | |
|---|---|---|---|
| 3,608,366 | 8/1969 | Tokita et al. | 73/99 |
| 3,672,212 | 6/1972 | Caspary et al. | 73/99 |

Primary Examiner—Jerry W. Myracle
Attorney, Agent, or Firm—Toren, McGeady and Stanger

[57] ABSTRACT

In a torsional oscillation apparatus, for example for testing plastics, a lower clamp is arranged in torsionally-fast or non-rotating manner, for one end of a test specimen, and an upper clamp is provided for the other end of the test specimen. The upper clamp is connected securely to the underside of an oscillatory body suspended from a thread or wire which is twistable in a substantially resistance-free manner. A tautening device exerts, on one of the clamps, a force which keeps the test specimen taut. A stimulating device provides stimulating torsional oscillations of the torsion pendulum formed by the test specimen and the oscillatory body, and a transducer, cooperating with the oscillatory body, produces electrical pulses corresponding to the torsional oscillation of the pendulum.

8 Claims, 9 Drawing Figures

TORSIONAL OSCILLATION APPARATUS

SUMMARY OF THE INVENTION

This invention relates to a torsional oscillation apparatus, for example for testing plastics, comprising a lower clamp, arranged in torsionally-fast or non-rotating manner, for one end of a test specimen, an upper clamp for the other end of the test specimen, which upper clamp is connected securely to the underside of an oscillatory body which is suspended from a thread or wire which is twistable in a substantially resistance-free manner, a tautening device which exerts, on one of the clamps, a force which keeps the test specimen taut, a stimulating device for stimulating torsional oscillations of the torsion pendulum formed by the test specimen and the oscillatory body, and a transducer, co-operating with the oscillatory body, for producing electrical pulses corresponding to the torsional oscillation of the pendulum.

Accurate measurement results are achieved with such apparatus only when the pendulum performs a pure torsional oscillation, i.e. only a rotary oscillation about its axis which is provided by the wire or thread. Any other oscillation components lead to measurement errors. In the known apparatus, the pendulum can, however, perform undesirable oscillating movements. More particularly, the pendulum can also oscillate transversely. Moreover, the oscillatory body itself can oscillate, like a balance beam, about the point at which it is connected to the wire or thread. Thus, when the oscillatory body is a bar, it can oscillate about a horizontal line at the centre of the bar; when the oscillatory body is a circular disc, it can oscillate about a horizontal line at the centre of the bar; when the oscillatory body is a circular disc, it can oscillate about random diameters of the disc. Incidental or accidential assymmetries of the test specimen, and/or of the clamping of the same, can result in the stimulating device stimulating not only torsional oscillations but also the undesired oscillations. As has been mentioned, this leads to measurement errors.

An object of the invention is, therefore, to provide an apparatus, of the type discussed at the introduction to this specification, in which the pendulum can perform only torsional oscillations.

The solution, in acccordance with the invention, to this object consists in that the thread or wire, adjacent its upper end, extends through an upper eye which is connected securely to the oscillatory body and, directly above the oscillatory body, extends through a lower eye which is connected securely to the upper end of the thread or wire.

In this construction, the pendulum has ony a single degree of freedom, namely that of a rotation about the pendulum axis coinciding with the wire or thread. The lower eye prevents transverse oscillation of the pendulum and the upper eye prevents the oscillatory body from oscillating like a balance beam.

The invention will be described further, by way of example, with reference to the accompanying drawings, in which.

Figure 5:
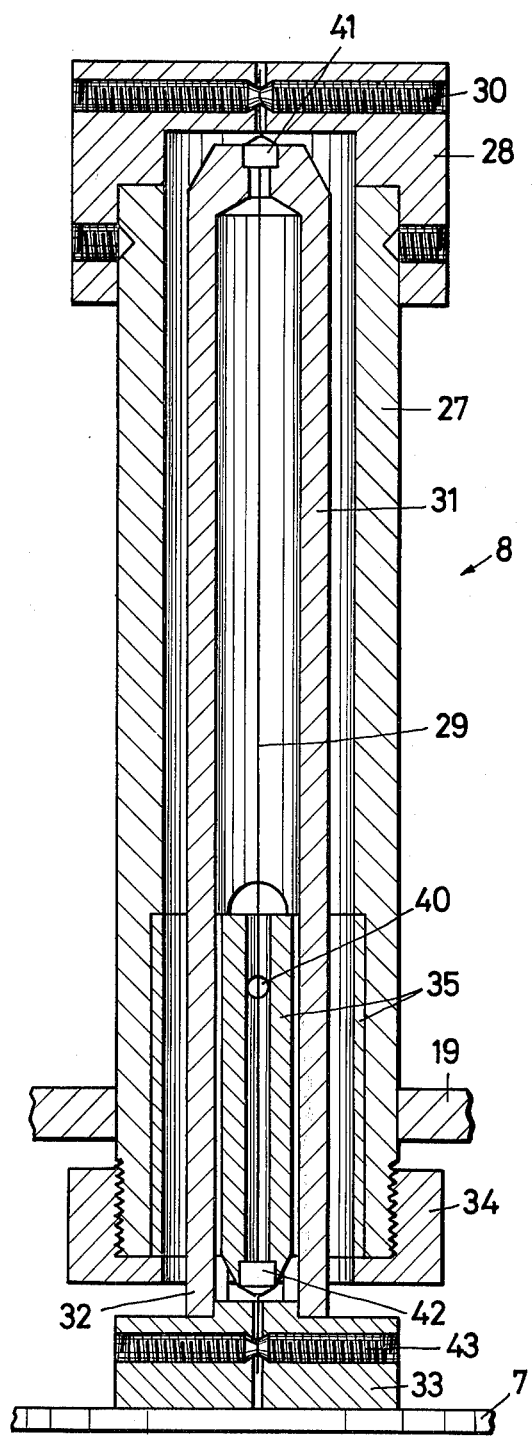
FIG. 5 is a longitudinal section through a sub-assembly of the apparatus of FIGS. 1 and 2, on an enlarged scale.
Figure 6:
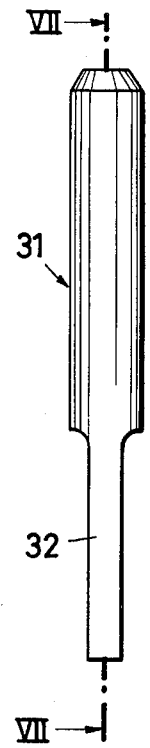
Figure 7:
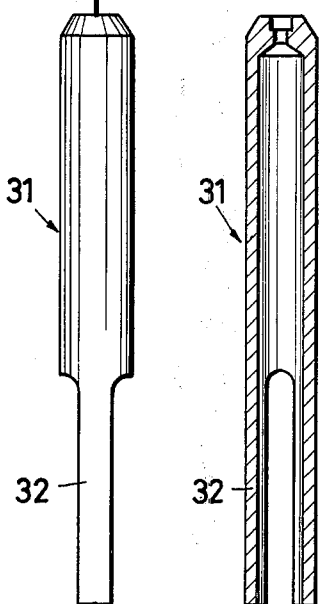
Figure 8:
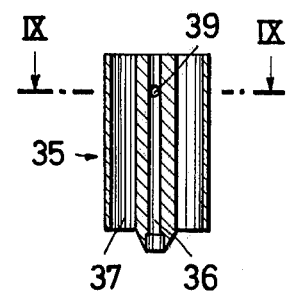
Figure 9:
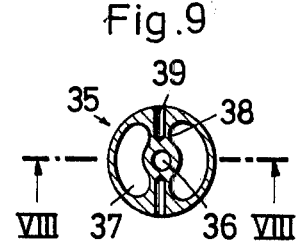

FIG. 6 s an elevation of a component part of the subassembly of FIG. 5, to a smaller scale than the latter;

FIG. 7 is a section taken along the line VII—VII of FIG. 6;

FIG. 8 is a longitudinal section through another component part of the sub-assembly of FIG. 5; to the same scale of FIGS. 6 and 7; and FIG. 9 is a section taken along the line IX—IX of FIG. 8.

Figure 1:
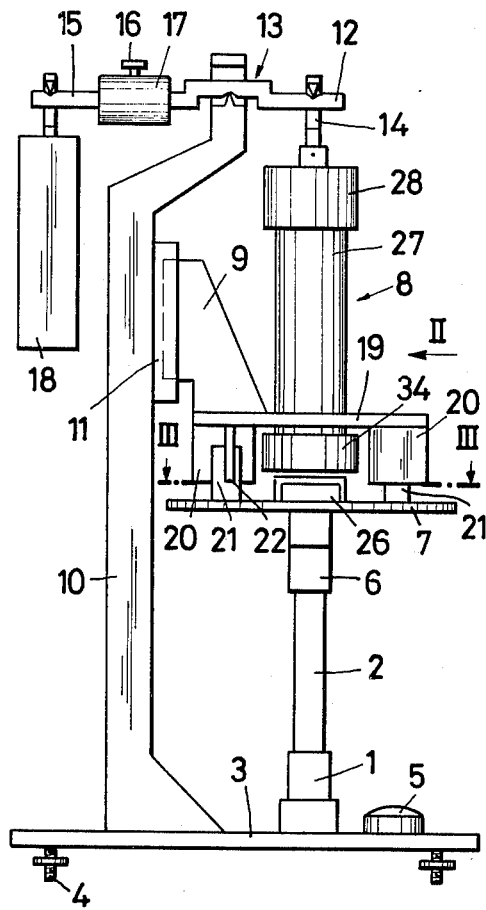
FIG. 1 is a schematic side view (taken in the direction of the arrow I in FIG. 2) of a preferred embodiment of the torsional oscillation apparatus, for example for testing plastics, in accordance with the invention.
Figure 2:
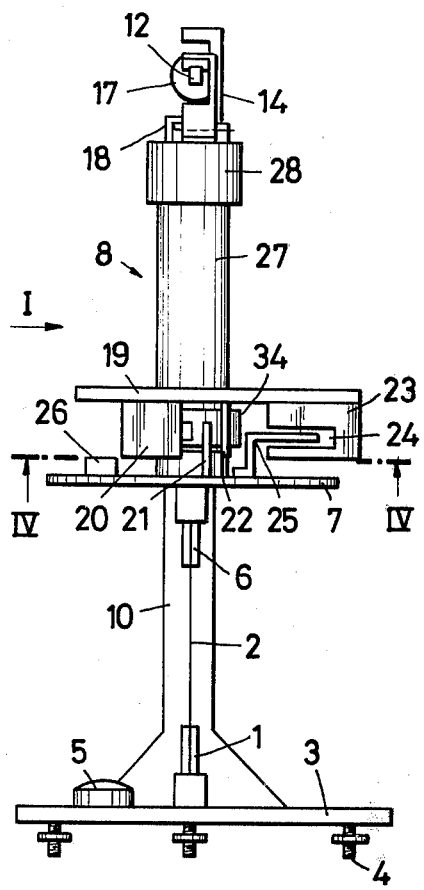
FIG. 2 is a front view taken in the direction indicated by the arrow II in FIG. 1.
Figure 3:
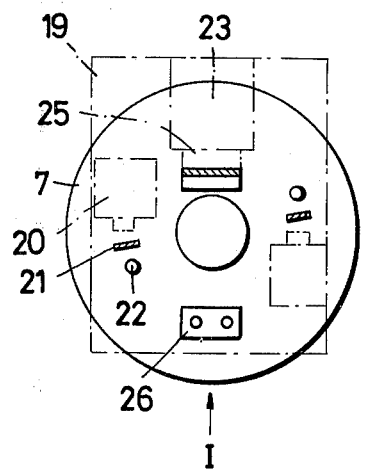
FIG. 3 is a sectional plan taken along the line III—III of FIG. 1, with certain parts lying above the sectional plane being shown in dot-dash lines.
Figure 4:
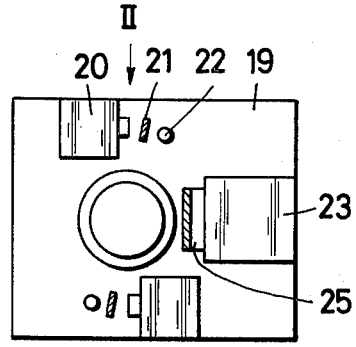
FIG. 4 is an underneath sectional plan taken along the line IV—IV of FIG. 2.

A preferred embodiment of the torsional oscillation apparatus of the invention, as shown in FIGS. 1 and 2, a comprising a lower clamp 1 for one end of a strip-form plastics test specimen 2. This lower clamp 1 is fastened on a base plate 3 the horizontal position of which is adjustable by means of three adjusting screws 4 and a levelling indicator or circular spirit level 5 for reasons explained further below. The upper end of the plastics strip 2 is clamped into an upper clamp 6 which is fastened to the underside of an oscillatory body in the form of a disc 7. The oscillatory disc 7 is suspended on a wire 29 (FIG. 5) which is not visible in FIGS. 1 and 2, which is twistable in a virtually resistance-free manner, and which is contained in a structural unit 8 which is described in more detail below with reference to FIGS. 5 to 9.

The structural unit 8 is mounted so as to be vertically displaceable, by means of a sliding carriage 9, on a column 10 which is fastened on the base plate 3. Guide 11, indicated only schematically, for the carriage 9, is virtually frictionless, being executed with rolling bearings.

The structural unit 8 is suspended from one arm 12 of a balance beam 13 by means of a connection member 14 which is hingedly connected both to the arm 12 and to the structural unit 8. The balance beam 13 is mounted at the upper end of the column 10. The other arm 15 of the balance beam 13 carries a sliding weight 17 which is displaceable along the arm 15, and can be fastened in place by means of a screw 16. At its free end, the arm 15 also carries a counter-weight 18. The weights 17 and 18 maintain the equilibrium of the structural unit 8 together with the carriage 9 and further parts connected therewith, inclusive of the oscillatory disc 7 and of the upper clamp 6, and it will be appreciated that the balance beam 13 and weights 17, 18 constitute a tautening device which exerts on the clamp 6, a force which keeps the specimen 2 taut.

The sliding weight 17 is so adjusted that in addition to maintaining the equilibrium of the structural unit 8 and the carriage 9 and the parts connect thereto, a small force is exerted on the plastics strip 2 just adequate to keep the latter taut, but noy sufficient to produce any appreciable tension in the strip 2.

The plastics strip 2, together with the oscillatory disc 7, forms a torsion pendulum the torsional body of which is constituted by the plastics strip 2, and the oscillatory body of which is the disc 7. In order to exert a torque for stimulating torsional oscillations of this pendulum 2, 7, two electromagnets 20 are fastened to a plate 19 which is connected to the carriage 9 and the structural unit 8. These two electromagnets 20 are diametrically opposed to one another with regard to the pendulum axis provided by the wire 29, and have equal spacings therefrom. Associated with each electromagnet 20 is a respective armature 21 which is fastened to the oscillatory disc 8. Pins 22 fastened to the plate 19 limit the possible rotary oscillation of the disc 7.

To produce electrical oscillations corresponding to the torsional oscillations of the pendulum 2, 7, a light source (not visible) is arranged in a housing 23, fastened to the plate 19, to one side of a slot 24 in the housing 23, and to the other side of the slot is a photosensitive element and a diaphragm. A shutter plate 25 connected to the oscillatory disc 7 projects into the slot 24. The light source, the photoelectric element, the diaphragm and details of the shutter plate 25 are not shown in the drawings.

To compensate for the weight of the shutter plate 25, the disc 7 carries a counter-weight 26.

As shown by FIG. 5, the structural unit 8 includes a hollow cylindrical housing 27 which is closed at the top and open at the bottom and which is fastened to the plate 19. The connection member 14 (not shown in FIG. 5) is pivotally connected to lid 28 of this housing. The wire 29 is clamped in the centre of the lid 28 by two clamping screws 30. The wire 29 extends along the cylinder axis of the housing 27.

Disposed coaxially in the housing 27 is an upwardly-closed sleeve 31 which is open at the bottom and is slotted or bifurcated to form two limbs 32. This sleeve 31 is shown in FIGS. 6 and 7 to a smaller scale than FIG. 5. The limbs 32 are connected securely to a footpiece 33 which is connected securely to the oscillatory disc 7.

Seated in the lower part of the housing 27 is a cylinder 35 which is held by means of a cap nut 34. This cylinder 35 has a central longitudinal bore 36, through which the wire 29 extends with a clearance all around, and two recesses 37 which penetrate the cylinder 35 lengthwise and which are kidney-shaped in the cylinder cross-section and lie opposite one another. The webs formed between the recesses 37 are designated by the reference numeral 38.

The cylinder 35 has two bores 39 for screws or pins 40 by which it is secured against rotation in the housing 27. Each limb 32 of the sleeve 31 engages through one of the recesses 37 of the cylinder 35 which all round clearance. This clearance is so dimensioned that, upon rotary oscillation of the oscillatory disc 7 connected securely to the sleeve 31, the limbs 32 of the sleeve 31 do not strike against the webs 38 of the cylinder 35 which is connected securely to the housing 27 and therewith also to the plte 19 and thus does not participate in the pendulum oscillation.

The wire 29 extends with a clearance of, for example, only 0.1 mm, below the lid 28 of the housing 27, through a narrow longitudinal bore of an eye 41 which is seated in the sleeve 31, and, similarly above the footpiece 33, through a longitudinal bore of a lower eye 42 which is seated in the cylinder 35. The longitudinal bores of these eyes 41 and 42 each have a diameter of, for example, 0.3 mm. In the footpiece 33, the wire 29 is fastened by clamping screws 43. The bores, receiving the wire 29, in the lid 28, and in the footpiece 33, are shown exaggeratedly large in FIG. 5; their diameter needs scarcely to exceed that of the wire 29.

The carriage guide 11 and the housing 27 are mounted so accurately at a right angle to the base plate 3 that the wire 29 extends freely through the eyes 41 and 42 when the base plate 3 is adjusted so as to be accurately horizontal with the aid of the adjusting screws 4 and the level 5. The rotary oscillation of the pendulum 2, 7, is then no hindered by the eyes 41 and 42. However, the pendulum can perform only rotary oscillation about the torsion axis formed by the wire 29, and no other oscillations. The lower eye 42 connected securely to the upper clamping location (30) of the wire 29 prevents transverse pendulum oscillations, and the upper eye 41 connected securely to the oscillatory disc 7 inhibit the oscillatory body 7 from oscillating like a balance beam about the lower clamping location 43 of the wire 29. In this way, also, wobbling oscillations of the disc 7 are prevented. Measuring erros which arise in known apparatus through undesired oscillation components are, therefore, reliably avoided in the arrangement of the invention. If the plastics strip 2, in the course of the plastics testing, should be caused to shrink or expand (e.g. as a result of cooling or heating in a tempering chamber, not shown, arranged under the oscillatory disc 7), it will remain taut under the action of the weights 17 and 18. Also the mutual positions both of the electromagnets 20 and of the armatures 21 and of the photoelectrical equipment in the housing 23 and of the diaphragm 25 remain unchanged, when the oscillatory body 7, following shrinkage or expansion of the plastics strip 2, moves downwards or upwards; this is because the plate 19 to which the electromagnets 20 and the housing 23 are fastened follows this movement, because all the parts 6, 7, 20, 21, 23 and 25 are carried by the carriage 9.

What we claim is:

1. A torsional oscillation apparatus, for example for testing plastics, comprising a lower clamp, arranged in torsionally-fast or non-rotating manner, for one end of a test specimen, an upper clamp for the other end of the test specimen, which upper clamp is connected securely to the underside of an oscillatory body which is suspended from a wire or thread which is twistable in a substantially resistance-free manner, a tautening device which exerts, on one of the clamps a force which keeps the test specimen taut, a stimulating device for stimulating torsional oscillations of the torsions pendulum formed by the test specimen and the oscillatory body, and a transducer, cooperating with the oscillatory body, for producing electrical pulses corresponding to the torsional oscillation of the pendulum, characterised in that the wire or thread, adjacent its upper end, extends through an upper eye which is connected securely to the oscillatory body and, directly above the oscillatory body, extends through a lower eye which is connected securely to the upper end of the wire or thread.

2. Apparatus as claimed in claim 1, characterised in that the lower clamp is arranged stationarily, and the upper end of the wire or thread as well as the lower eye are carried by a vertically-displaceable carriage to which the tautening device applies an upwardly-directed force which exceeds the weight of the carriage and of the parts carried thereby by the force which serves to keep the test specimen taut.

3. Apparatus as claimed in claim 2, characterised in that the tautening device comprises a balance beam to one arm of which the carriage is pivotally connected and the other arm of which is weighted.

4. Apparatus as claimed in claim 3, characterised in that said other arm is weighted by a weight which is adjustable in its position along said other arm for adjusting the force which serves to keep the test specimen taut.

5. Apparatus as claimed in claim 2, characterised in that the parts, not connected to the oscillatory body, of the stimulating device and of the transducer are connected securely to the carriage.

6. Apparatus as claimed in claim 1, characterised in that the upper eye is arranged at the upper end of a sleeve the wall of which is bifurcated at the bottom to form two diametrically opposed limbs which are connected securely to the oscillatory mass, and in that the lower eye is formed at the lower end of a cylinder which is connected securely to the upper clamping point of the wire or thread and which has a central longitudinal bore through which the wire or thread extends with clearance all round spacing, and two recesses penetrating the cylinder, which recesses are kidney-shaped in the cylinder cross-section and are opposite one another, and through which extend the respective limbs of the sleeve, with a clearance which permits rotary oscillation of the sleeve relative to the cylinder.

7. Apparatus as claimed in claim 6, characterized in that the sleeve is arranged, with radial clearance, in a cylindrical housing in a lid of which the upper end of the wire or thread is fastened, which housing is connected at its bottom, securely to the cylinder, and in that the tautening device acts on the housing.

8. Apparatus as claimed in claim 7, characterized in that the lower claim is arranged stationarily and the cylindrical housing is carried by a vertically displaceable carriage to which the tautening device applies an upwardly-directed force which exceeds the weight of the carriage and of the parts carried by the force which serves to keep the specimen taut.

* * * * *